United States Patent [19]
Kurihara et al.

[11] Patent Number: 5,763,161
[45] Date of Patent: Jun. 9, 1998

[54] ASSAY METHOD OF TESTING FOR THE PRESENCE OF CYTOMEGALOVIRUS ANTIGEN

[75] Inventors: Takashi Kurihara; Junko Hayashi; Akio Ito, all of Ibaraki; Takayoshi Asai, Chiba, all of Japan

[73] Assignee: Yuka Medias Co., Ltd., Ibaraki, Japan

[21] Appl. No.: 577,248

[22] Filed: Dec. 22, 1995

[30] Foreign Application Priority Data

May 26, 1995 [JP] Japan ................................ 7-128072

[51] Int. Cl.⁶ .......................... C12Q 1/70; G01N 33/53; G01N 33/567
[52] U.S. Cl. ........................ 435/5; 435/7.1; 435/7.2; 435/7.21; 435/7.94
[58] Field of Search .................... 435/5, 7.1, 7.2, 435/7.21, 7.94

[56] References Cited

PUBLICATIONS

Harlow, et al.: Antibodies a laboratory manual:pp. 8, 361–366, 390, 392–393, 400–402, and 406–407, 1988.

Journal of Medical Virology, vol. 25, pp. 179–188, 1988, Wim Van Der Bij, et al., "Rapid Immunodiagnosis of Active Cytomegalovirus Infection by Monoclonal Antibody Staining of Blood Leucocytes".

Transplant International, vol. 2, pp. 147–164, 1989, W.J. Van Son, et al., "Cytomegalovirus Infection After Organ Transplantation: An Update With Special Emphasis On Renal Transplantation".

Transplantation, vol. 48, No. 6, pp. 991–995, Dec. 1989, A.P. Van Den Berg, et al., "Cytomegalovirus Antigenemia As A Useful Marker of Symptomatic Cytomegalovirus Infection After Renal Transplantation–A Report of 130 Consecutive Patients".

The Journal of Infectious Diseases 1991, vol. 164, pp. 265–270, 1991, A.P. Van Den Berg, et al., "Antigenemia in the Diagnosis and Monitoring of Active Cytomegalovirus Infection After Liver Transplantation".

Journal of Clinical Microbiology, vol. 30, No. 11, pp. 2822–2825, Nov. 1992, A. Erice, et al., "Cytomegalovirus (CMV) Antigenemia Assay Is More Sensitive Than Shell Vial Cultures for Rapid Detection of CMV in Polymorphonuclear Blood Leukocytes".

The Journal of Infectious Diseases, vol. 166, pp. 683–684, 1992, J.M.M. Grefte, et al., "Cytomegalovirus Antigenemia Assay: Identification of the Viral Antigen as the Lower Matrix Protein PP65".

Bone Marrow Transplantation, vol. 9, pp. 247–253, 1992, A.M. Vlieger, et al., "Cytomegalovirus Antigenemia Assay or PCR Can Be Used to Monitor Ganciclovir Treatment in Bone Marrow Transplant Recipients".

Annals of Internal Medicine, vol. 118, pp. 173–178, 1993, J.M. Goodrich, et al., "Ganciclovir Prophylaxis to Prevent Cytomegalovirus Disease After Allogenic Marrow Transplant".

Biotest Bulletin, vol. 5, pp. 63–72, 1993, G. Bein, et al., "Cytomegalovirus Infection in Transplantation Medicine. Current Diagnostic Approaches With Special Emphasis on the PP65 Antigenemia Assay".

*Primary Examiner*—Lynette F. Smith
*Assistant Examiner*—Brett Nelson
*Attorney, Agent, or Firm*—Oblon, Spivak, McClelland, Maier & Neustadt, P.C.

[57] ABSTRACT

Disclosed are a method for testing for the presence of a cytomegalovirus antigen by using an antibody which specifically recognizes cytomegalovirus Lower matrix protein pp65, as a primary antibody, which comprises using an alkaline phosphatase-labeled antibody as a secondary antibody and a method for testing for the presence of a cytomegalovirus antigen which comprises using an alkaline phosphatase-labeled antibody which specifically recognizes cytomegalovirus Lower matrix protein pp65, or (Fab')$_2$ or Fab' fragment of the antibody which specifically recognizes cytomegalovirus Lower matrix protein pp65 as a primary antibody.

10 Claims, 2 Drawing Sheets

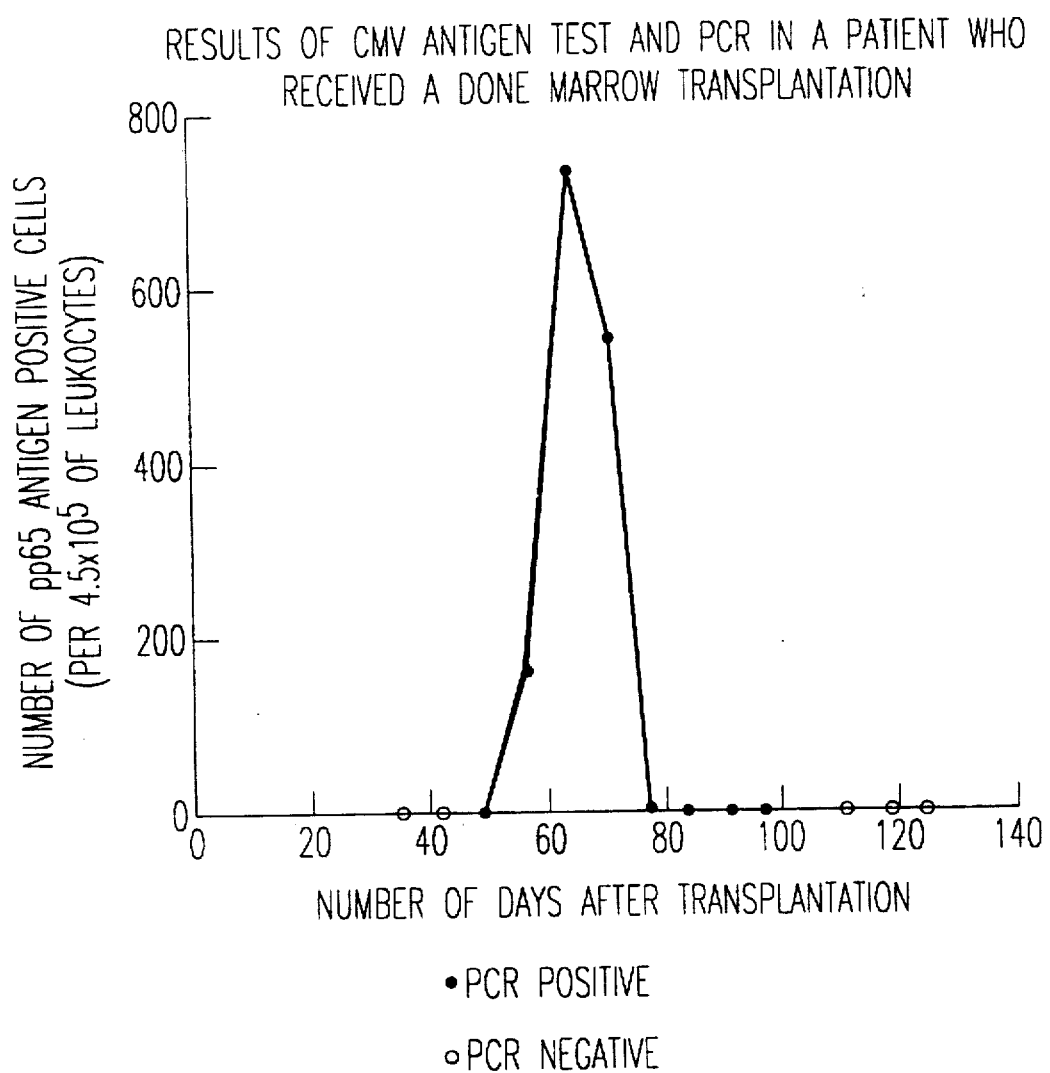

ASSAY METHOD OF TESTING FOR THE PRESENCE OF CYTOMEGALOVIRUS ANTIGEN

BACKGROUND OF THE INVENTION

1. Field of the invention

This invention relates to an assay method of testing a cytomegalovirus antigen by using an alkaline phosphatase-labeled antibody.

2. Prior art

In patients under immunosuppression due to transplantation of bone marrow, kidney, liver or heart and acquired immunodeficiency syndrome (AIDS), infectious diseases caused by active cytomegalovirus (hereinafter sometimes referred to as "CMV") cause extremely serious and various complications. In patients who receive a kidney transplant, 40 to 70% of the patients suffer from active CMV infectious diseases, and 10 to 20% of the infected patients show clinical symptoms such as interstitial pneumonia, persistent fever and gastroenteritis (Transplant Int. 2, pp. 147 to 164, 1989). In recent years, as a therapeutic agent of active CMV infectious diseases showing such clinical symptoms, use of a ganciclovir preparation has been approved, and significant effects on retinitis and enteritis have been obtained. Further, it has been reported that although a therapeutic effect of a ganciclovir preparation on pneumonia after bone marrow transplantation is not sufficient, effectiveness is improved by using an immunoglobulin preparation in combination (Bone Marrow Transplantation 9, pp. 247 to 253, 1992). On the other hand, it has been reported that ganciclovir has side effects such as neutropenia, thrombocytopenia and reversible central nervous disorders depending on its dosage (Ann. Intern. Med. 118, pp. 173 to 178, 1993), and also from economical standpoint, a suitable administration plan of ganciclovir is required to be investigated. Therefore, in clinical fields, it is an important task to diagnose, in an early stage and with certainty, whether various symptoms such as interstitial pneumonia and persistent fever in a patient who received a transplant are caused by cytomegalovirus or other bacteria or virus, or caused based on rejection (Biotest Bulletin 5, pp. 63 to 72, 1993).

In the prior art, for diagnosis of CMV infectious diseases, there have been carried out virus separation, a shell vial assay (SVA), a globulin type specific serological test and DNA diagnosis by PCR. In 1988, Van der Bij et al. found that monoclonal antibodies (C10 and C11) prepared by using CMV (AD169 strain)-infected fibroblasts as an immunogen are suitable for detecting cytomegalovirus Lower matrix protein (hereinafter sometimes referred to as "pp65 antigen") appeared in leukocytes of a patient who received a kidney transplant, and further reported that diagnostic results and clinical symptoms of such an antigen-testing method are correlated to those of virus separation and enzyme-linked immunosorbent assay (ELISA) (J. Med. Virol. 25, pp. 179 to 188, 1988, J. Infect. Dis. 166, pp. 683 and 684, 1992). Since then, a method of testing a CMV antigen by using anti-pp65 antibodies (C10 and C11) has been positioned as a useful index of active CMV infectious diseases (Transplantation 48, pp. 991 to 995, 1989, J. Infect. Dis. 164, pp. 265 to 270, J. Clin. Microbiol. 30, pp. 2822 to 2825).

As the method of testing a CMV antigen by using anti-pp65 antibodies (C10 and C11), there may be generally mentioned a method in which separated peripheral blood leukocytes are fixed on a slide glass by CYTOSPIN™ (trade name, produced by Shandon Co.); an anti-pp65 antibody and a labeled secondary antibody are reacted in this order; and observation and judgment are carried out under an optical microscope after color formation reaction when the secondary antibody is labeled with enzyme, or under fluorescence microscope when the secondary antibody is labeled with fluorescence. As the labeled secondary antibody, there has been used a peroxidase (hereinafter sometimes referred to as "POD")-labeled secondary antibody and a fluorescence-labeled secondary antibody. However, labeling with POD has a problem of nonspecific staining by endogenous POD, and for labeling with fluorescence, an expensive fluorescence microscope and an expensive anti-fading reagent are required. Therefore, the method of testing a CMV antigen by using a POD-labeled or fluorescence-labeled antibody is not suitable as a routine test method in clinical fields.

SUMMARY OF THE INVENTION

An object of the present invention is to provide an assay method of testing a CMV antigen, which is not influenced by nonspecific staining caused by endogenous POD activity, does not require an expensive apparatus such as a fluorescence microscope and can provide judgment simply, easily and accurately.

The present inventors have studied intensively in consideration of the situation as described above and consequently established an assay method of testing a CMV antigen by using an alkaline phosphatase (hereinafter referred to as "ALP") as a labeling material of a primary or secondary antibody, as an assay method of testing a CMV antigen, which is not influenced by nonspecific staining caused by endogenous POD activity, does not require an expensive apparatus such as a fluorescence microscope and can provide judgment simply, easily and accurately. Further, by using the above assay method of testing a CMV antigen, active CMV infectious diseases can be found rapidly and accurately.

That is, the present invention relates to an assay method of testing a cytomegalovirus antigen by using an antibody which specifically recognizes cytomegalovirus Lower matrix protein pp65 (hereinafter sometimes referred to as "anti-pp65 antibody"), as a primary antibody, which comprises using an ALP-labeled anti-species-specific immunoglobulin antibody as a secondary antibody (two step method) or using an ALP-labeled anti-pp65 antibody as a primary antibody (one step method).

BRIEF DESCRIPTION OF THE DRAWINGS

FIG. 3 shows results of a CMV antigen test and PCR in a patient who received a bone marrow transplant.

DESCRIPTION OF THE PREFERRED EMBODIMENTS

In the following, the present invention is explained in detail.

As a living body component to be used in the antigen test of the present invention, there may be mentioned leukocytes separated from blood, alveolar washing (BAL), nasal mucus, sputum and urine, but leukocytes separated from blood are generally used. Separation of leukocytes can be carried out by a known dextran method or centrifugation method. Separated leukocytes can be adhered to a slide glass by a cytospin method or an adsorption method. The specimen slide thus prepared is fixed by using, for example, acetone, methanol, acetone/methanol or formalin, and the pp65 antigen can be exposed on the slide glass without impairing the shapes of the leukocytes. As the most preferred fixing conditions, there may be mentioned fixing by using acetone/methanol at −20° to 4° C. for 30 seconds to 10 minutes or fixing by using 0.5 to 5% formalin at 4° to 25° C. for 30 seconds to 20 minutes.

Figure 1:
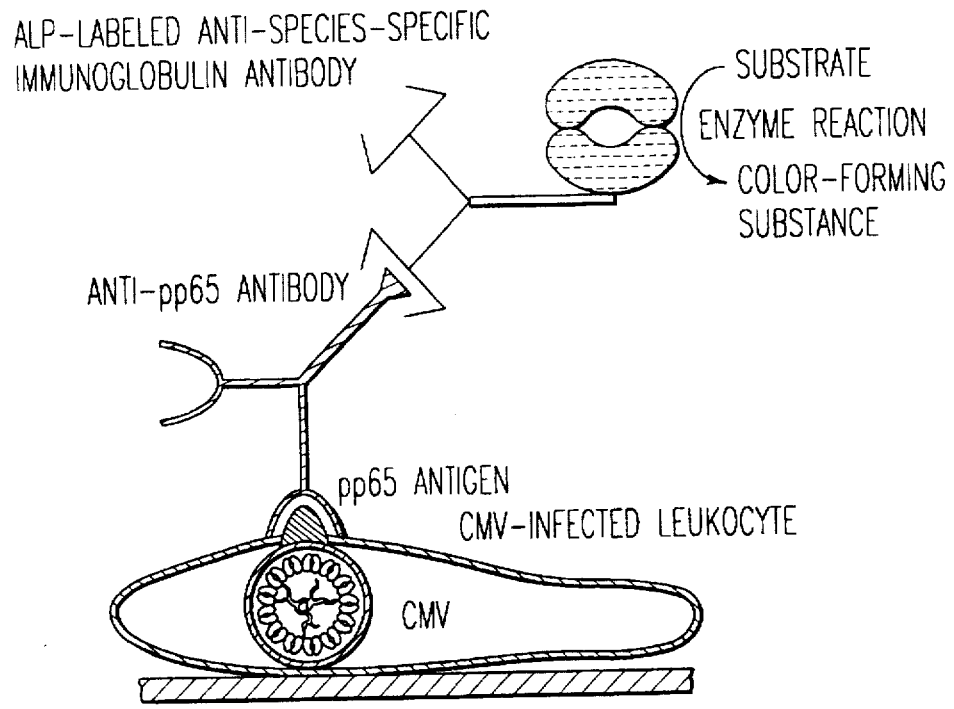
FIG. 1 shows an assay method of testing a CMV antigen by using an anti-pp65 antibody as a primary antibody and an ALP-labeled anti-species-specific immunoglobulin antibody as a secondary antibody according to a two step method.

First, a two-step reaction shown in FIG. 1 is explained below.

The anti-pp65 antibody to be used as a primary antibody in the present invention can be prepared by, for example, the method of Van der Bij et al. (J. Med. Viol. 25, 1988). The anti-pp65 antibody obtained may be used as such or purified by a known purification method such as protein A affinity chromatography, ion exchange chromatography, gel chromatography and electrophoresis. In order to prevent non-specific staining in immune staining, the antibody may be converted into (Fab')$_2$ or Fab' (i.e., F(ab')$_2$ fragment or F(ab') fragment), if necessary. The purified or unpurified anti-pp65 antibody obtained can be used for immune staining by diluting it with a suitable buffer solution or physiological saline. As the buffer solution to be used, there may be mentioned a TRIS hydrochloride buffer solution (hereinafter referred to as "TBS") and a maleate buffer solution. For the purpose of preventing nonspecific staining, to the above antibody-diluted solution, BSA, casein, γ-globulin and serums of various animals such as serums of goat, horse, sheep and rabbit may be added as a blocking agent. Further, a nonionic, cationic or anionic surfactant such as TWEEN 20™ (trade name, produced by Atlas Powder Co.), TRITON X-100™ (trade name, produced by Rohm & Haas Co.) and NP-40™ (trade name, produced by Sigma Chemical Co.) may be added.

In immune staining, 20 to 150 μl of the anti-pp65 antibody solution is used per specimen slide and reacted at 4° to 37° C. for 10 minutes to 4 hours. After the reaction, the specimen slide is washed with a washing liquid at 4° C. to room temperature for 30 seconds to 40 minutes to remove an unreacted antibody which is not bound to the pp65 antigen. As the washing liquid which can be used, there may be mentioned physiological saline, TBS and purified water. To the washing liquid, a nonionic, cationic or anionic surfactant such as TWEEN 20™, TRITON X-100™ and NP-40™ as mentioned above may be added in order to improve washing efficiency and prevent the slide from being dried. Next, as a secondary antibody, an antibody to the primary antibody labeled with ALP, a cocktail antibody thereof or an antiserum thereof (an anti-species-specific immunoglobulin antibody) is reacted. For example, when a monoclonal antibody is used as a primary antibody, an anti-mouse immunoglobulin antibody (antiserum) is used, and when a rabbit antiserum is used as a primary antibody, an anti-rabbit immunoglobulin antibody (antiserum) is used. The ALP-labeled antibody, the cocktail antibody and the antiserum can be prepared by, for example, binding ALP to an antibody purified by affinity chromatography, by using glutaraldehyde and then applying the solution thereof to gel filtration chromatography to remove an unreacted antibody and ALP. The antibody to be labeled may be converted into (Fab')$_2$ or Fab'. The ALP-labeled antibody, the cocktail antibody and the antiserum thus obtained can be used in immune staining by diluting them with a suitable buffer solution or physiological saline in the same manner as in the primary antibody. As the reaction conditions of the secondary antibody, there may be mentioned reaction conditions of at 4° to 37° C. for 10 minutes to 4 hours.

Figure 2:
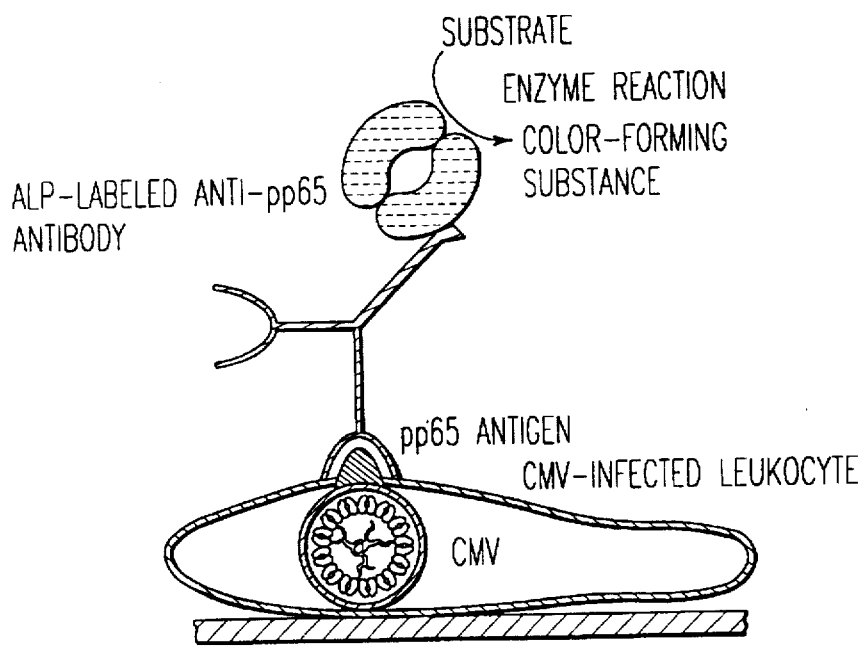
FIG. 2 shows an assay method of testing a CMV antigen by using an ALP-labeled anti-pp65 antibody as a primary antibody according to a one step method.

Immune staining can be carried out by one step reaction as shown in FIG. 2 using an anti-pp65 antibody labeled with ALP or an anti-pp65 antibody converted into (Fab')$_2$ or Fab' in place of the two step reaction using the primary antibody and the secondary antibody described above. As a method of preparing the above ALP-labeled antibody, there may be mentioned, for example, a method in which a purified anti-pp65 antibody is converted into Fab', and the thiol group at the Fab' hinge portion is reacted with ALP into which a maleimide group is introduced. In place of the maleimide group, a pyridyldisulfide group may be introduced. The ALP-labeled anti-pp65 antibody can be used for immune staining by diluting it with a suitable buffer solution or physiological saline. For the purpose of preventing non-specific staining, to the above antibody-diluted solution, BSA, casein, γ-globulin and serums of various animals such as serums of goat, horse, sheep and rabbit may be added as a blocking agent. Further, a nonionic, cationic or anionic surfactant such as TWEEN 20™, TRITON X-100™ and NP-40™ as mentioned above may be added. As the reaction conditions, there may be mentioned reaction conditions of at 4° to 37° C. for 10 minutes to 4 hours. After the reaction, the specimen slide is washed to remove an unreacted antibody. As a washing liquid, there may be mentioned physiological saline, a TRIS hydrochloride buffer solution and purified water. To the washing liquid, a nonionic, cationic or anionic surfactant such as TWEEN 20™, TRITON X-100™ and NP-40™ as mentioned above may be added.

Next, color formation reaction is carried out by adding a substrate of ALP. The substrate may be any substrate so long as it is a substrate for ALP which is generally used in immune staining. There may be mentioned, for example, a New Fuchsin color-forming substrate, BCIP/NBT and a Fast Red color-forming substrate. It is preferred to use a New Fuchsin color-forming substrate since color is not faded for a long time. As the reaction conditions at this time, there may be mentioned reaction conditions of at 4° to 37° C. for 10 minutes to 1 hour. After the color formation reaction, in order to facilitate observation, comparative staining may be carried out with hematoxylin. The slide is sealed by using a sealing agent such as a HSR™ solution (trade name, produced by Midori Juji Co.) and gelatin, and stained leukocytes having CMV pp65 antigen can be observed and counted by an optical microscope.

The above immune staining can be carried out semi-automatically or automatically by using a commercially available immune staining apparatus in addition to the above manual operation. In that case, it is preferred to suitably adjust the amounts of the primary antibody and the secondary antibody to be used.

Abbreviations used in the present specification are shown below.

PCR: polymerase chain reaction, PBS: a salt-added phosphate buffer solution, TBS: a salt-added TRIS buffer solution, BSA: bovine serum albumin, BCIP/NBT: 5-bromo-4-chloro-3-indoxylphosphate/nitroblue tetrazolium chloride, SDS-PAGE: sodium dodecylsulfate-polyacrylamide gel electrophoresis, EDTA: ethylenediaminetetraacetic acid, and PNPP: p-nitro-phenylphosphoric acid.

EXAMPLES

The present invention is described in detail by referring to Examples. However, the following Examples should be regarded as a help to obtain specific recognition of the present invention and do not limit the range of the present invention.

Example 1

(1) Separation of leukocytes and preparation of specimen slide 1 ml of 5% dextran-PBS was added to 4 ml of peripheral blood collected with EDTA of a patient who received a bone marrow transplant and infected with active CMV, and the mixture was incubated at 37° C. for 15 minutes. After the supernatant was subjected to centrifugation of 200×g at room temperature for 8 minutes, the sediment was suspended by adding 3 ml of a hemolyzing reagent (0.83% $NH_4Cl$, 0.1% $KHCO_3$, 0.0037% EDTA·2Na) thereto, and the suspension was reacted on ice for 5 minutes. After the reaction was terminated by adding 3 ml of physiological saline to the suspension, centrifugation and washing with physiological saline were repeated three times, and the concentration of leukocytes was finally adjusted to $1.5 \times 10^6$ leukocytes/ml. 100 μl of the above suspension was subjected to cytospinning (550 rpm, 5 minutes) by using CYTOSPIN™ (trade name, produced by Shandon Co.) to prepare a specimen slide. The specimen slide was air-dried at room temperature for 30 minutes, fixed with cold acetone/methanol (1:1) for 90 seconds and air-dried at room temperature overnight.

(2) Immune staining

After the fixed specimen slide was dipped in 0.01% Tween 20 (trade name, produced by Atlas Powder Co.)-containing physiological saline (hereinafter referred to as "ST"), 50 μl of a Clonab CMV (trade name, produced by Biotest, an anti-pp65 antibody-C10 and C11 cocktail) solution was added to the specimen and reacted at room temperature for 1 hour. After the slide was washed with ST twice, 50 μl of an ALP-labeled anti-mouse immunoglobulin antibody solution was added to the slide and reacted at room temperature for 1 hour. The slide was washed with ST twice and then subjected to color formation by using New Fuchsin substrate system (room temperature, 15 minutes). Comparative staining was carried out with hematoxylin, and the slide was sealed by a HSR™ solution (trade name, produced by Midori Juji Co.). Under an optical microscope, 243 characteristic positive cells having nuclei stained in red to purplish red were observed per $1.5 \times 10^5$ leukocytes.

Example 2

(1) Separation of leukocytes and preparation of specimen slide 1 ml of 5% dextran-PBS was added to 4 ml of peripheral blood collected with EDTA of a patient who received a bone marrow transplant and infected with active CMV, and the mixture was incubated at 37° C. for 15 minutes. After the supernatant was subjected to centrifugation of 200×g at room temperature for 8 minutes, the sediment was suspended by adding 3 ml of a hemolyzing reagent (0.83% $NH_4Cl$, 0.1% $KHCO_3$, 0.0037% EDTA·2Na) thereto, and the suspension was reacted on ice for 5 minutes. After the reaction was terminated by adding 3 ml of physiological saline to the suspension, centrifugation and washing with physiological saline were repeated three times, and the concentration of leukocytes was finally adjusted to $1.5 \times 10^6$ leukocytes/ml. 100 μl of the suspension was subjected to cytospinning (550 rpm, 5 minutes) by using CYTOSPIN™ (trade name, produced by Shandon Co.) to prepare a specimen slide. The specimen slide was air-dried at room temperature for 30 minutes, fixed with PBS containing 1% formalin and 2% sucrose for 10 minutes and washed with PBS containing 1% bovine fetal serum four times. The slide was further washed with PBS containing 0.5% NP-40™ (trade name, produced by Sigma Chemical Co.), 10% sucrose and 1% bovine fetal serum, washed with PBS containing 1% bovine fetal serum four times, finally washed with purified water for 15 seconds and air-dried at room temperature for 1 hour.

(2) Immune staining

The specimen slide was subjected to immune staining in the same manner as in Example 1 (2) and observed under an optical microscope to find 250 positive cells per $1.5 \times 10^5$ leukocytes.

Example 3

(1) Preparation of ALP-labeled anti-pp65 antibody Fab'

1) Preparation of anti-pp65 antibody (Fab')$_2$ 40 ml of a buffer solution for binding was added to 40 ml of a culture supernatant containing an anti-pp65 antibody. The mixture was applied to Protein A™ column (trade name, produced by Toso Co.) which had been equilibrated previously, and then washed with a buffer solution for binding. A buffer solution for elution was flown, and the eluate was collected by separation. The solution was concentrated by ULTRACENT 30™ (trade name, produced by Toso Co.) and substituted by 1×PBS. To the concentrate was added a 1/50 amount of 5% sodium azide, and the mixture was stored at 4° C. (yield: 1.12 mg). By using SDS-PAGE (silver staining), purification purity was confirmed. Next, the purified antibody was digested with pepsin at 37° C. for 24 hours, and completion of the reaction was confirmed by SDS-PAGE (disappearance of a band corresponding to a heavy chain). The reaction mixture was subjected to gel filtration using SUPEROSE 12™ (trade name, produced by Pharmacia Co.) to collect an antibody fraction. The antibody fraction was concentrated by ULTRACENT 30™ (trade name, produced by Toso, Co.) and substituted by a 0.1M sodium phosphate buffer solution (pH 6) containing 5 mM EDTA (yield: 593 μg).

2) Preparation of anti-pp65 antibody Fab'

To 620 μl of the anti-pp65 antibody (Fab')$_2$ was added 68 μl of a 0.1M 2-mercaptoethylamine solution (a 0.1M sodium phosphate buffer solution (pH 6) containing 5 mM EDTA) (hereinafter referred to as "MEA"), and the mixture was reduced at 37° C. for 90 minutes. The reaction mixture was purified by gel filtration using Superose 12 (trade name, produced by Pharmacia Co.) and then concentrated by Ultracent 30 (trade name, produced by Toso Co.) (yield: 415 μg).

3) Preparation of ALP into which a maleimide group is introduced 0.5 ml of ALP (10 mg/ml) was applied to NAP5™ (trade name, produced by Pharmacia Co.) which had been equilibrated previously. Subsequently, 1 ml of an eluent was added to ALP, and 1 ml of an eluate fraction was collected on ice. To the fraction was added 2 mg of SULFO SMCC™ (trade name, produced by Pierce Co.), and the mixture was subjected to reaction for introducing a maleimide group at 30° C. for 2 hours. The reaction mixture was subjected to gel filtration using Superose 12 (trade name, produced by Pharmacia Co.) to remove unreacted Sulfo-SMCC (trade name, produced by Pierce Co.) (yield: 4.4 mg).

4) Preparation of ALP-labeled anti-pp65 antibody Fab'

To 140 μl of the anti-pp65 antibody Fab' (1.41 mg/ml) was added 140 μl of ALP (11.9 mg/ml) to which a maleimide group had been introduced, and the mixture was reacted at 4° C. for 3 days. The reaction was terminated by adding 10 mM MEA. Production of the desired ALP-labeled anti-pp65 antibody Fab' was confirmed by polyacrylamide gel electrophoresis and the Western blotting method. After 280 μl of the reaction mixture obtained above was purified by gel filtration using SUPEROSE 12™ (trade name, produced by Pharmacia Co.) and then concentrated by ULTRACENT 30™ (trade name, produced by Toso Co.), the buffer solution was substituted by 1×TBS (pH 7.6). Thereafter, the concentrate was applied to a rabbit anti-mouse immunoglobulin antibody (produced by Dako Co.)-fixed CH CEPHALOSE 4B™ (trade name, produced by Pharmacia Co.) which had been equilibrated by a 0.1M TRIS buffer solution (pH 7) containing 1 mM magnesium chloride and 0.1 mM zinc chloride. The fraction eluted by the same buffer solution (pH 9.5) was collected by separation (recovered amount: 1.5 ml). Elution of the desired labeled antibody was confirmed by measuring ALP activity using PNPP as a substrate. Finally, the eluate was concentrated by ULTRACENT 30™ (trade name, produced by Toso Co.), the buffer solution was replaced with 1×TBS, and the antibody obtained was stored at 4° C. (yield: 208 μl).

(2) Evaluation of properties of ALP-labeled anti-pp65 antibody Fab'

The ALP-labeled anti-pp65 antibody Fab', prepared in the above (1) was diluted with 1×TES containing 1% human serum so that the concentration of the antibody Fab' was adjusted to 10 μg/ml. 50 μl of the diluted ALP-labeled antibody solution was added to a positive control slide, a negative control slide and specimen slides prepared from specimens of patients who received a bone marrow transplant and infected with active CMV (MW1 to MW3), and reacted at room temperature for 1 hour. After the slides were washed with ST twice, 50 μl of a New Fuchsin color-forming solution was added to the slides to effect color formation reaction at room temperature for 15 minutes. After the slides were washed with ST twice, 50 μl of a hematoxylin solution was added to the slides and reacted at room temperature for 3 minutes. The slides were washed with purified water twice, air-dried and sealed by using a HSR™ solution (trade name, produced by Midori Juji Co.). Under an optical microscope, the number of positive cells showing red to purplish red characteristic nucleus-stained images were counted and represented by the number of positive cells per 1.5×10⁵ leukocytes. The results are shown in Table 1.

TABLE 1

| Immune staining | Specimen name | Number of positive cells | Staining strength |
|---|---|---|---|
| One step method | Positive control | A large number | Strong |
| | Negative control | 0 | None |
| | MW1 | >1000 | Strong |
| | MW2 | 391 | Strong |
| | MW3 | 1 | Strong |
| Two step method | Positive control | A large number | Strong |
| | Negative control | 0 | None |
| | MW1 | >1000 | Strong |
| | MW2 | 300 | Strong |
| | | 319 | Strong |
| | | 312 | Strong |
| | MW3 | 5 | Strong |
| | | 1 | Strong |

(Note) One step method means a direct ALP antibody method using an ALP-labeled anti-pp65 antibody Fab', and Two step method means an immune staining method using an anti-CMV pp65 antibody as a primary antibody and an ALP-labeled antibody as a secondary antibody.

Example 4

Monitoring of CMV infectious diseases in a patient who received a bone marrow transplant By using EDTA blood from the 35th day to 125th day after transplantation collected from a patient who received a bone marrow transplant due to chronic myelocytic leukemia, a CMV antigen test was conducted according to the method of Example 1. As a result, one positive cell per 4.5×10⁵ leukocytes was observed in the blood on the 49th day after transplantation; the most 730 positive cells were observed on the 63rd day; the number of positive cells started to reduce; and the test result became negative on the 84th day (see FIG. 3). In the DNA test according to the PCR method, the test result became positive on the 49th day after transplantation and became negative on the 112nd day (see FIG. 3).

By using the assay method of testing a cytomegalovirus antigen of the present invention, an accurate and rapid test can be carried out without receiving influence of nonspecific staining. By establishment of the assay method of testing a cytomegalovirus antigen, a useful diagnostic test method of cytomegalovirus infected diseases can be provided, and by tracing the number of positive cells, therapy of active cytomegalovirus infected diseases can be monitored.

What is claimed is:

1. A method for testing for the presence of Cytomegalovirus antigen in a sample comprising the following steps in order:
   (i) preparing a sample slide and fixing the sample,
   (ii) adding a primary antibody which specifically recognizes Cytomegalovirus Lower matrix protein pp65, to form an immune complex of antigen and primary antibody,
   (iii) washing the sample slide with a surfactant-containing washing liquid to remove unreacted primary antibody,
   (iv) adding a secondary antibody which is directly labeled with alkaline phosphatase derived from an animal different from that of the primary antibody to form an immune complex of antigen, primary antibody and secondary antibody,
   (v) washing the sample slide with a surfactant-containing washing liquid to remove unreacted secondary antibody,
   (vi) adding a substrate for alkaline phosphatase to form a colored substance thereby staining the immune complex formed in step (iv), and (vii) detecting positive cells having stained-nucleus in the sample.

2. The method according to claim 1, wherein the primary antibody is an Fab' fragment of an antibody which specifically recognizes the Cytomegalovirus Lower matrix protein pp65, obtained by digesting said antibody with pepsin and reducing the resulting (Fab')2 fragment.

3. The method according to claim 1, wherein the substrate for alkaline phosphatase is selected from the group consisting of New Fucsin color-forming substrate, BCIP/NBT and Fast Red color forming substrate.

4. The method according to claim 1, wherein the primary antibody is an anti-pp65 antibody-C10 and C11 cocktail and the secondary antibody is an anti-mouse immunoglobulin antibody.

5. The method according to claim 1, wherein the surfactant is selected from the group consisting of Tween 20, Triton X-100 and NP-40.

6. A method for testing for the presence of Cytomegalovirus antigen in a sample comprising the following steps in order:

(i) preparing a sample slide and fixing the sample, (ii) adding a primary antibody which specifically recognizes Cytomegalovirus Lower matrix protein pp65 and which is directly labeled with alkaline phosphatase for form an immune complex of antigen and primary antibody, (iii) washing the sample slide with a surfactant-containing washing liquid to remove unreacted primary antibody, (iv) adding a substrate for alkaline phosphatase to form a colored substance thereby staining the immune complex formed in step (ii), and (v) detecting positive cells having stained-nucleus in the sample.

7. The method according to claim 6, wherein the primary antibody is an Fab' fragment of an antibody which specifically recognizes Cytomegalovirus Lower matrix protein pp65, obtained by digesting said antibody with pepsin and reducing the resulting (Fab')2 fragment.

8. The method according to claim 6, wherein the substrate for alkaline phosphatase is selected from the group consisting of New Fucsin color-forming substrate, BCIP/NBT and Fast Red color forming substrate.

9. The method according to claim 6, wherein the primary antibody is an anti-pp65 antibody-C10 and C11 cocktail and the secondary antibody is an anti-mouse immunoglobulin antibody.

10. The method according to claim 6, wherein the surfactant is selected from the group consisting of Tween 20, Triton X-100 and NP-40.

* * * * *